US008912332B2

(12) United States Patent
Maison et al.

(10) Patent No.: US 8,912,332 B2
(45) Date of Patent: Dec. 16, 2014

(54) SYNTHESIS OF TRIVALENT FLEXIBLE FRAMEWORKS WITH LIGANDS COMPRISING CATECHOL UNITS FOR FUNCTIONALIZING SURFACES

(75) Inventors: Wolfgang Maison, Wetzlar (DE); Faiza Khalil, Mücke (DE); Elisa Franzmann, Wettenberg-Wißmar (DE)

(73) Assignee: Justus-Liebig-Universitaet Giessen, Giessen (DE)

(*) Notice: Subject to any disclaimer, the term of this patent is extended or adjusted under 35 U.S.C. 154(b) by 0 days.

(21) Appl. No.: 13/821,650

(22) PCT Filed: Sep. 7, 2011

(86) PCT No.: PCT/EP2011/065483
§ 371 (c)(1),
(2), (4) Date: Jun. 4, 2013

(87) PCT Pub. No.: WO2012/032085
PCT Pub. Date: Mar. 15, 2012

(65) Prior Publication Data
US 2013/0245270 A1   Sep. 19, 2013

(30) Foreign Application Priority Data

Sep. 10, 2010   (EP) .................................... 10176289

(51) Int. Cl.
| C07C 233/18 | (2006.01) |
| C07D 217/04 | (2006.01) |
| C07C 231/14 | (2006.01) |
| C07C 237/06 | (2006.01) |
| C07C 231/02 | (2006.01) |
| C07C 237/08 | (2006.01) |
| C07C 271/22 | (2006.01) |

(52) U.S. Cl.
CPC ............ *C07C 233/18* (2013.01); *C07C 231/14* (2013.01); *C07C 237/06* (2013.01); *C07C 231/02* (2013.01); *C07C 237/08* (2013.01); *C07C 271/22* (2013.01)
USPC ........................... 546/141; 564/153; 562/478

(58) Field of Classification Search
None
See application file for complete search history.

(56) References Cited

U.S. PATENT DOCUMENTS 6,479,198 B2 * 11/2002 Makino et al. ................ 430/17
2008/0247984 A1   10/2008 Messersmith et al.

FOREIGN PATENT DOCUMENTS

| WO | WO-2005/118831 | 12/2005 |
| WO | WO-2010/037044 | 4/2010 |

OTHER PUBLICATIONS

R. Stonard, et al., "Linear Peptide Alkaloids From the Sponge *Cliona celata* (Grant). Celenamides C and D", *Canadian Journal of Chemistry*, 58(20):2121-26 (1980).
J. Young, et al., ""Smart" Cascade Polymers. Modular Syntheses of Four-Directional Dendritic Macromolecules with Acidic, Neutral, or Basic Terminal Groups and the Effect of pH Changes on Their Hydrodynamic Radii", *Macromolecules*, 27:3464-71 (1994).
Henry, et al., "New 8-Hydroxyguinoline and Catecholate Iron Chelators: Influence of Their Partition Coefficient on Their Biological Activity", *Biochemical Pharmacology*, 62:1355-62 (2001).
K. Yoon, et al., "Monofunctionalization of Dendrimers with Use of Microwave-Assisted 1, 3-Dipolar Cycloadditions", *Organic Letters*, 9(11):2051-54 (2007).
J. Wach, et al., "Antimicrobial Surfaces Through Natural Product Hybrids", *Angew. Chem. Int Ed.*, 47:7123-26 (2008).
M. Kleinert, et al., "A Modular Approach for the Construction and Modification of Glyco-SAMs Utilizing 1,3-dipolar Cycloaddition", *Org. Biomol. Chem.*, 6:2118-32 (2008).
S. Sahoo, et al., Complexation of a Tripodal Amine-Catechol Ligand Tris((2,3- dihydroxybenzylamino)ethyl)amine Towards Al(III), Ga(III), and In(III), *Monatsh Chem.*, 140:139-45 (2009).
M. Wyszogrodzka, et al., "Study of Single Protein Adsorption onto Monoamino Oligoglycerol Derivatives: A Structure-Activity Relationship", *Langmuir*, 25(10):5703-12 (2009).
International Search Report in International Application No. PCT/EP2011/065483 issued/mailed on Jan. 19, 2012, 6 pages.

* cited by examiner

*Primary Examiner* — Zinna Northington Davis
(74) *Attorney, Agent, or Firm* — Marshall, Gerstein & Borun LLP

(57) ABSTRACT

The present invention describes tripodal catechol derivatives with a flexible basic framework for the functionalization of surfaces, and methods for their production and use. The central atom of the flexible framework is hereby a tertiary aliphatic carbon atom. The remaining fourth bridgehead position is easily suitable to be further functionalized via so-called click reactions, e.g. with biomolecules, dyes, radiomarkers, polyethylene glycol or active agents.
The compounds according to the present invention have the general formula X—C[(CH$_2$)$_n$—YZ]$_3$, wherein X stands for a group —(CH$_2$)$_p$—R$^5$, wherein p=0 to 10 and R$^5$ is selected from —H, —NH$_2$, —NO$_2$, —OH, —SH, —O—NH$_2$, —NH—NH$_2$, —N═C═S—, —N═C═O—, —CH═CH$_2$, —C≡CH, —COOH, —(C═O)H, —(C═O)R$^6$ Y stands for —CH$_2$—, —CH═CH—, —C≡C—, —O—, —S—, —S—S—, —NH—, —O—NH—, —NH—O—, —HC═N—O—, —O—N═CH—, —NR$^1$—, -Aryl-, -Heteroaryl-, —(C═O)—, —O—(C═O)—, —(C═O)—O—, —NH—(C═O)—, —(C═O)—NH—, —NR$^1$—(C═O)—, —(C═O)—NR$^1$—, —NH—(C═O)—NH—, —NH—(C═S)—NH—, R$^1$ stands for an aryl group, R$^6$ for an alkyl, alkenyl, alkynyl, aryl or heteroaryl group, and Z stands for a catechol derivative.
The production of the compounds occurs by reacting a compound X—C[(CH$_2$)$_n$—Y']$_3$ with a reagent Y"Z to the corresponding compound X—C[(CH$_2$)$_n$—YZ]$_3$ and subsequent purification of the reaction product.
Y' and Y" are hereby precursors of Y. The compounds according to formula (I) according to the present invention are suitable to be used in a method to functionalize surfaces. The X group of the compounds according to the present invention is suitable to be optionally coupled to an effector, for example, by means of click chemistry.

18 Claims, No Drawings

SYNTHESIS OF TRIVALENT FLEXIBLE FRAMEWORKS WITH LIGANDS COMPRISING CATECHOL UNITS FOR FUNCTIONALIZING SURFACES

CONTINUING DATA

This is the U.S. national phase of PCT/EP2011/065483 filed Sep. 7, 2011, which claims the benefit of EP 1017289.6 filed Sep. 10, 2010.

BACKGROUND OF THE INVENTION

1. Field of the Invention

The present invention relates to the fields of organic chemistry and material sciences.

2. Brief Description of Related Technology

The state of the art recognises numerous methods for the functionalisation of surfaces. Such functionalisations are used in order to modify the material properties of the surfaces in a targeted manner. Such functionalisations should be as durable as possible and allow for a highly defined loading of the surface.

In the field of medical technology, special importance is place on functionalised surfaces. Implants should—by way of example in the dental industry and orthopedics (joint replacement)—be as biocompatible as possible, i.e. by not have, inter alia, having a tendency towards biofouling, not causing any inflammatory reactions and not being seeded with pathogenic microorganisms. Furthermore, they must permanently resist to heavy mechanical strain.

Medical implants frequently comprise frequently the metals iron and/or titanium, while dental implants also contain apatite. Until now, monomeric derivatives of the catecholamine have been used as a surface binder to which different functional molecules such as antibiotics or PEG were subsequently bonded. With such conjugates, it was possible to detect an increased resistance of the surfaces against biofouling. Polymer structures which imitate mussel adhesion proteins are an alternative to monomeric catechol derivatives. These are used as a biomimetic adhesive.

With the help of monomeric catechol derivatives, metal surfaces are suitable to be easily functionalised; however this functionalisation unfortunately comes with low durability. This is particularly disadvantageous in the case of heavy material stress such as applications in the dental industry. Although polymer structures allow for an extremely strong connection, they do not allow for a targeted or defined functionalisation of the surface as is desired, by way of example, for implants.

Methods suitable to coat antimicrobially surfaces with natural product hybrids are described in J-Y Wach, S Bonazzi, K Gademann: "Antimikrobielle Oberflächen durch Naturstoffhybride" (Antimicrobial surfaces by means of natural product hybrids), 120, 7232-7235. The natural product hybrids only comprise monomeric catecholamines.

Examinations with regard to structure-activity relationships of methylated or hydroxyterminated polyglycerol structures, which were deposited as SAMs on surfaces of gold, are described in M Wyszogrodzka, R Haag: "Study of Single Protein Adsorption onto Monoamino Oligoglycerol Derivatives: A Structure-Activity Relationship", Langmuir 2009, 25, 5703-5712. The shown dendritic polyglycerol structures do not comprise any aromatic functional groups.

In J K Young, G R Baker, G R Newkome: "Smart Cascade Polymers. Modular Syntheses of Four-Directional Dendritic Macromolecules with Acidic, Neutral, or Basic Terminal Groups and the Effect of ph Changeson their Hydrodynamic Radii", Macromolecules 1994, 27, 3464-3471 examples for the synthesis of fourdirectional, flexible and dendritic cascade polymers are described. The disclosed dendritic molecules, however, do not comprise any catecholamine groups, in a manner characteristic of mussel adhesion proteins.

In K Yoon, P Goyal, M Weck: "Monofunctionalization of Dendrimers with Use of Microwave-Assisted 1,3-Dipolar Cycloadditions", Org Lett 2007, 9, 2051-2054, are also described methods for the production of flexible dendritic compounds. The work discloses, inter alia, the introduction of cyclic functional groups via 1,3-dipolar cycloadditions. M Kleinert, T Winkler, A Terfort and T B Lindhorst describe in "A modular approach for the construction and modification of glyco-SAMs utilizing 1,3-dipolar cycloaddition", Org Biomol Chem 2008, 6, 2118-2132 also methods for the modular synthesis of flexible dendritic compounds. In addition to 1,3 dipolar cycloadditions are also described click reactions on SAMs.

In S K Sahoo, B K Kanungo, M Baral:, Complexation of a tripodal amine-catechol ligand tris(2,3-dihydroxybenzylamino)ethyl)amine towards Al(III), Ga(III), and In(III), Monatsh Chem 2009, 140, 139-145 trivalent flexible frameworks with catecholamine ligands are described. The trivalent flexible frameworks are tertiary aliphatic amines, and the catecholamines have a 2,3 dihydroxy substitution pattern. The disclosed compounds do not allow for a functionalisation with effectors, and are therefore only in a limited way usable for the functionalisation of surfaces. When the compounds are used as metal chelators no additional functionality, for instance for the cell or pathogenic recognition, is suitable to be introduced.

SUMMARY OF THE INVENTION

The present invention provides, in contrast, trivalent flexible frameworks with ligands comprising catechol units. The design of the compounds hereby occurs biometrically and is oriented towards mussel adhesion proteins and siderophores, which naturally cause high affinity bindings to surfaces. The compounds according to the present invention comprise tripodal flexible frameworks with one tertiary aliphatic carbon atom to which three catechol units are bonded. The remaining fourth substituent of the tertiary carbon atom is easily suitable to be further functionalised via so-called click reactions, e.g. with biomolecules, dyes, radiomarkers, polyethylene glycol or active agents.

DETAILED DESCRIPTION

The aim of the present invention is to provide compounds which allow for a durable functionalisation and a highly defined loading of surfaces, and methods for the production of these compounds.

The present invention describes tripodal catechol derivatives with a flexible basic framework for the functionalisation of surfaces, and methods for their production and use. The central atom of the flexible framework is hereby a tertiary aliphatic carbon atom. The design of the compounds hereby occurs biometrically and is oriented towards mussel adhesion proteins and siderophores, which naturally cause high affinity bindings to surfaces. A fourth remaining position of the flexible framework is suitable to be optionally functionalised by so-called click reactions, for example with biomolecules, polyethylene glycol or active agents.

The task, namely to provide compounds which allow for a durable functionalisation and a highly defined loading of surfaces is achieved according to the present invention via compounds according to formula (I):

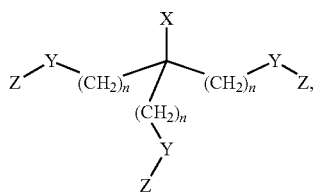

(I)

wherein
n is an integer between 0 and 10,
Y is selected from —CH$_2$—, —CH=CH—, —C≡C—, —O—, —S—, —S—S—, —NH—, —O—NH—, —NH—O—, —HC=N—O—, —O—N=CH—, —NR1-, -Aryl-, -heteroaryl-, —(C=O)—, —O—(C=O)—, —(C=O)—O—, —NH—(C=O)—, —(C=O)—NH—, —NR1-(C=O)—, —(C=O)—NR1-, —NH—(C=O)—NH—, —NH—(C=S)—NH—, wherein R$^1$ stands for a linear alkyl group with 1 to 10 C atoms or for a branched or cyclic alkyl group with 3 to 100 atoms,
Z is selected from

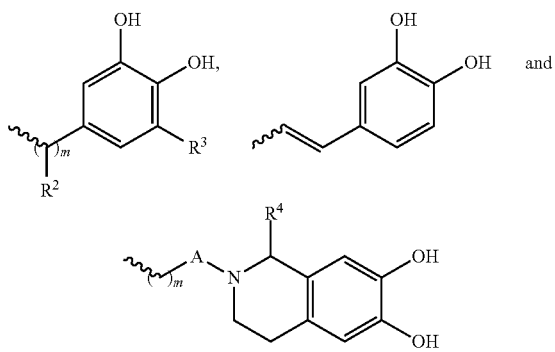

with
m=an integer between 0 and 10,
R$^2$=—H, —OH or —COOH,
R$^3$=—H, —OH
A=no atom or —(C=O)—
R$^4$=—H or

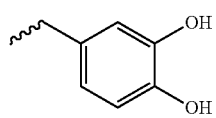

and
X stands for a group —(CH$_2$)$_p$—R$^5$, wherein p=0 to 10 and R$^5$ is selected from —H, —NH$_2$, —OH, —SH, —NO$_2$, —O—NH$_2$, —NH—NH$_2$, —N=CS, —N=C=O, —CH=CH$_2$, —C≡CH, —COOH, —(C=O)H, —(C=O)R$^6$, wherein the hydroxy, thio, amino or C=O groups are optionally suitable to be protected by a protective group, —N$_3$, —OR$^6$, —COOR$^6$, —NHR$^6$, —NR$^6$R$^7$, —CO—NHR$^6$, —CONR$^6$R$^7$, —NH—CO—R$^6$, 4-(2,5-dioxopyrrol-1-yl), wherein R$^6$ and R$^7$ stand independently of one another for a linear alkyl group with 1 to 10 C atoms, a linear alkenyl or alkynyl group with 2 to 10 C atoms, a branched alkyl, alkenyl or alkynyl group with 3 to 10 C atoms or a cyclic alkyl or alkenyl group with 3 to 10 C atoms, or X stands for a branched alkyl, alkenyl or alkynyl group with 3 to 10 C atoms or a cyclic alkyl, alkenyl or alkynyl group with 3 to 10 C atoms or for an aryl or heteroaryl group, wherein, in the event that X is a branched alkyl, alkenyl and alkynyl group, a cyclic alkyl or alkenyl group, an aryl or heteroaryl group, one C atom of this group X is optionally suitable to carry one group R$^5$ according to the definition above.

The compounds according to the present invention, the method for their production and the use of these compounds are explained hereinafter.

The invention is not limited to one of the embodiments described hereinafter; rather, it is suitable to be modified in various different ways.

All of the characteristics and advantages originating from the claims, description and figures (including constructive details, spatial arrangements and processing steps) are suitable to be essential to the invention, both in themselves and in the most various combinations.

The compounds according to formula (I) according to the present invention allow for a durable functionalisation and a highly defined loading of surfaces. Surfaces which are suitable to be functionalised and loaded comprise metals, metal oxides, apatite, glass and mixtures thereof. The term "apatite" hereby comprises both compounds following the general formula Ca$_5$(PO$_4$)$_3$(F,Cl,OH), in which the concentration of fluoride, chloride and hydroxyl ions is freely exchangeable, and the single minerals fluoroapatite, chloroapatite and hydroxylapatite.

Under "highly defined loading" is understood that the loading of the surface allows for a gap-free coating of the material in the form of a monolayer. "Monolayer" is understood to mean a layer of molecules according to the present invention on the surface which has a height of just a single molecule. A "functionalisation" is the addition of functional groups to the surface of a material via chemical synthesis methods. A coating of surfaces with the compounds according to the present invention thus represents a functionalisation of these surfaces. An effector molecule is optionally suitable to be bonded to the group X. This represents another functionalisation. An effector is a molecule or a molecule component which causes a physical, chemical, biochemical or biological process or controls, activates or inactivates such an effect. Examples for effectors are dyes, radioactive molecules, biomolecules such as amino acids, sugar, peptides, proteins, DNA, RNA, polymers such as ethylene glycol and derivatives thereof as well as active agents. Substances are referred to as active agents if they cause a specific effect or a reaction in low doses within an organism.

Due to the multivalent binding of the compounds according to formula (I), this functionalisation is durable in comparison to molecular exchange processes on the surface (such as the hydrolysis of the coupling in aqueous media) and also in comparison to mechanical strain.

In the context of the present invention, alkyl groups with 1 to 10 carbon atoms are selected from methyl, ethyl, n-propyl, isopropyl, 1-butyl, 2-butyl, tert-butyl, 1-pentyl, 2-pentyl, 3-pentyl, 3-methylbutyl, 2,2-dimethylpropyl, and all the isomers of hexyl, heptyl, octyl, nonyl and decyl. Alkenyl and alkynyl groups comprise at least two carbon atoms. They are selected from ethenyl and ethinyl groups and all isomers of propenyl, butenyl, pentenyl, hexenyl, heptenyl, octenyl, nonenyl, decenyl, ethinyl, propinyl, butinyl, pentinyl, hexinyl, heptinyl, octinyl, noninyl and decinyl groups. Branched alkyl, alkenyl and alkynyl groups comprise at least three carbon atoms and are selected according to the present invention from the aforementioned homologs with this minimum number of carbon atoms.

It is known to persons skilled in the art that cyclic alkyl and alkenyl groups have to comprise at least three carbon atoms. In the context of the present invention, "annular" groups are understood to mean such groups in which all carbon atoms are involved in the ring formation. Furthermore, "cyclic" groups are suitable to also comprise acyclic carbon atoms. In the context of the present invention, annular alkyl and alkenyl groups are propyl, butyl, pentyl, hexyl, heptyl, octyl, nonyl, decyl, propenyl, butenyl, pentenyl, hexenyl, heptenyl, octenyl, nonenyl and decenyl rings. If the groups X, $R^6$ and/or $R^7$ are cyclic alkyl or alkenyl groups, they are selected from the aforementioned annular alkyl and alkenyl groups which do not carry further substituents, and from the aforementioned annular alkyl and alkenyl groups which are themselves bonded to one or several acyclic alkyl, alkenyl or alkynyl groups. In the latter case, the binding of the cyclic alkyl or alkenyl group to the C1 atom of the adamantane skeleton (provided that the cyclic group represents X) or to the respective atom of the group $R^5$ (provided that the cyclic group represents $R^6$ or $R^7$) is suitable to occur via a cyclic or acyclic carbon atom of the cyclic alkyl or alkylene group. According to the above definition of the term "alkyl group", cyclic alkyl groups also comprise a total of 10 carbon atoms maximum.

According to the present invention, the group X is a group —(CH$_2$)$_p$—$R^5$. If $R^5$ is —NH2, —OH, —SH, —O—NH$_2$, —NH—NH—COOH, —(C=O)H, —(C=O)$R^6$, these groups are optionally suitable to be protected by a protective group. Protective groups for hydroxy, thiol, amino, carbonyl and carboxyl groups are known by persons skilled in the art. They are able to use these protective groups, i.e. to introduce and, if required, cleave them off again, without leaving the scope of protection of the patent claims.

By way of non-exhaustive example the following protective groups are to be named:
- for the OH group: methoxy methyl ether (MOM), β-methoxy ethoxy methyl ether (MEM), silyl ether, 2-tetrahydropyranyl (THP), Acetyl (Ac), benzoyl (Bz), benzyl (Bn, Bnl), dimethoxytrityl (DMT), methoxytrityl (MMT), p-methoxy benzyl ether (PMB), methylthiomethyl ether, pivaloyl (piv), methylether, ethoxyethyl ether (EE)
- for the SH group: tert-butyl, 2-tetrahydropyranyl, acetyl, 2-nitropyranyl, phenacyl, (cumarin-4-yl)methyl
- for the NH$_2$ group: 1-(1-adamantyl)-1-methoxycarbonyl (ADPOC), allyl-oxycarbonyl (ALLOC), benzyloxycarbonyl (abbreviated by Z or Cbz), 9-fluorenylmethoxycarbonyl (FMOC), p-methoxybenzyl carbonyl (Moz, MeOZ), tert-butyloxycarbonyl (BOC), acetyl (ac), benzoyl (Bz), benzyl (Bn, Bnl), p-methoxybenzyl (PMB), 3,4-dimethoxybenzyl (DMPM), p-methoxyphenyl (PMP), Tosyl (ts), sulfonamides
- for the carbonyl group (in aldehydes and ketones): the reaction with diols to acetals or ketals
- for the COOH group: methylester, benzyl ester, tert-butyl ester, silyl ester, orthoester, oxazolines According to the present invention, aryl groups are understood to mean phenyl, naphthyl and anthracenyl groups.

Heteroaryl groups are selected from furanyl, pyrrolyl, thiophenyl, imidazolyl, pyrazolyl, triazolyl, thiazolyl, oxazolyl, isooxazolyl, one oxadiazolyl, pyridinyl, pyrazinyl, pyrimidinyl, pyridazinyl, one triazinyl, one tetrazinyl, 1,4-dioxinyl, one thiazinyl, one oxazinyl, one azepinyl, a diazepinyl, benzofuranyl, isobenzofuranyl, indolyl, isoindolyl, benzothiophenyl, benzo[c]thiophenyl, benzimidazolyl, purinyl, indazolyl, benzoxazolyl, benzisoxazolyl, benzothiazolyl, quinolinyl, isochinolinyl, chinoxalinyl, acridinyl, chinazolinyl and cinnolinyl.

If Y stands for "-aryl-" or "-heteroaryl-", two carbon atoms of this aryl or heteroaryl group are connected with the alkylene groups —(CH$_2$)$_n$ or —(CH$_2$)$_m$ according to formula (I) and the definition of Z.

In an advantageous embodiment, Y is selected from no atom, —CH$_2$—, —NH—(C=O)—, —(C=O)—NH—, —NR$^1$—, wherein R$^1$ is as defined above.

In another advantageous embodiment, n is an integer between 0 and 3.

In another advantageous embodiment, m is an integer between 0 and 3.

Particularly advantageously, n and m stand independently of one another for integers between 0 and 3.

In a further advantageous embodiment, Z is a group

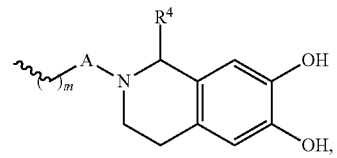

wherein m, A and $R^4$ are defined as above. Advantageously, m is hereby an integer between 0 and 3.

In a particularly advantageous embodiment, the group YZ is selected from

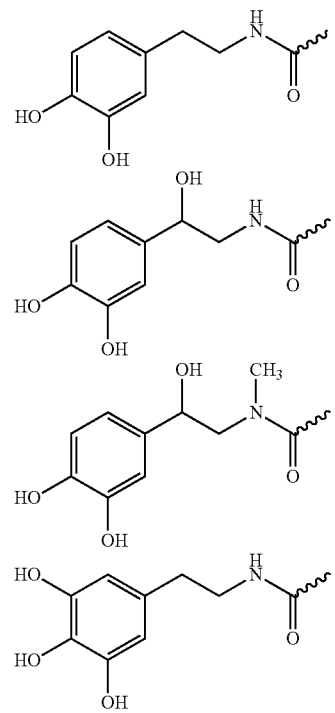

are derived from the following catechol derivatives:

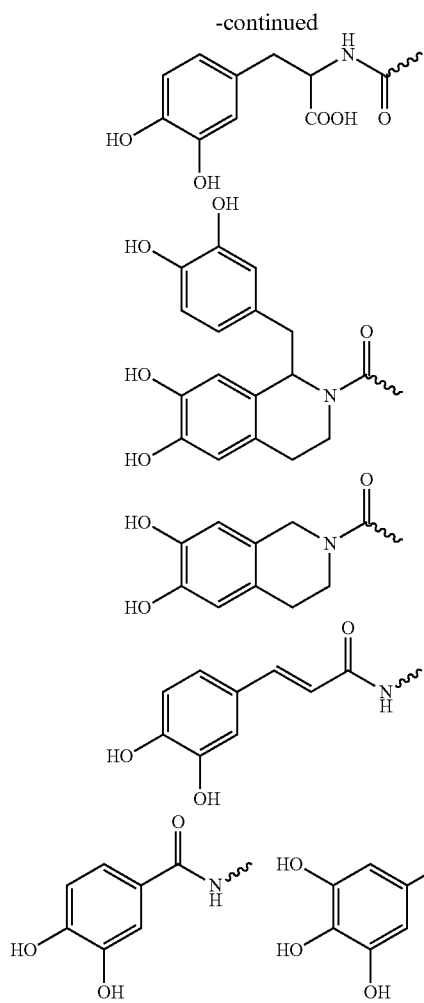

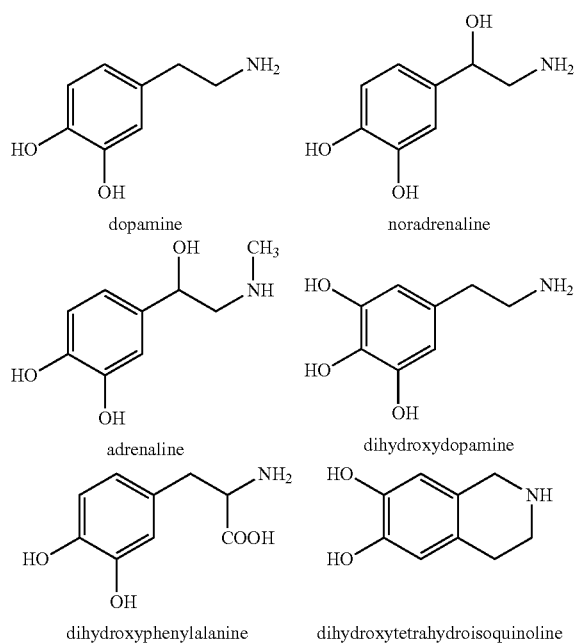

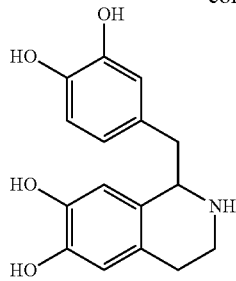

1-(3,4-dihydroxybenzyl)-
1,2,3,4-tetrahydroisoquinoline-6,7-diol

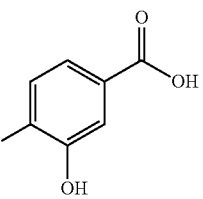

3,4-dihydroxy-
benzoic acid

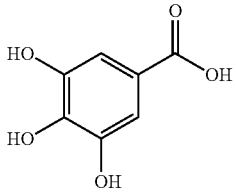

gallic acid

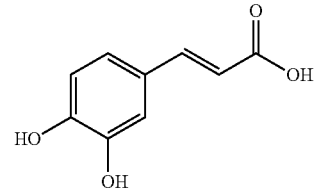

3,4-dihydroxycinnamic acid

In the context of the present invention, the compounds dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline and 3,4-dihydroxybenzoic acid are referred to as "catechol derivatives".

In a further advantageous embodiment, X represents a group (—$CH_2$)$_p$—$R^5$, wherein p represents an integer between 0 and 3 and $R^5$ is defined as in claim 1.

In a further advantageous embodiment, X stands for —($CH_2$)$_p$—$R^5$, wherein $R^5$ is selected from —H, —OH, —NH2, —$NO_2$, —NH—NH2, —$NHR^6$, —$NR^6R^7$, —O—NH2, —NH—(C=O)—C≡CH, —C≡CH, —N=C=S, —N=C=O, —COOH, —(C=O)H, —(C=O)$R^6$ and wherein p represents an integer between 0 and 3, and $R^6$ and $R^7$ are as defined above.

The compounds according to the present invention according to formula (I) are produced by reacting a compound X—C[($CH_2$)$_n$—Y']$_3$ with a reagent Y"Z to the corresponding compound X—C[($CH_2$)$_n$—YZ]$_3$ and by subsequent purification of the reaction product, wherein C stands for the tertiary aliphatic carbon atom and Y' for a precursor of the group Y according to formula (I), and wherein X, Z and n are defined as in formula (I).

Precursor is hereby understood to refer to a functional group which is converted via reaction with another functional group acting as precursor or a further reagent acting as precursor into a functional group according to formula (I).

Compounds of the formula X—C[($CH_2$)$_n$—Y']$_3$ are known. Persons skilled in the art are able to commercially purchase them or produce them independently with the help of their specialist knowledge following known synthesis procedures.

In an advantageous embodiment, X is a hydrogen atom.

In another advantageous embodiment, X is a group —($CH_2$)$_p$—$R^5$, wherein p represents an integer between 0 and 3, and $R^5$ is selected from —OH, —$NH_2$, —$NO_2$, —NH—$NH_2$, —$NHR^6$, —$NR^6R^7$, —O—$NH_2$, —NH—(C=O)—C≡CH, —C≡CH, —N=C=S, —N=C=O, —COOH, —(C=O)H, —(C=O)$R^6$, wherein $R^6$ and $R^7$ are defined as in formula (I). As already indicated, these groups may be optionally protected via a protective group (Pg). If these groups are protected, this occurs before the reaction with the reagent Y"Z, so that in this case Pg-X—C[(CH$_2$)$_p$—Y']$_3$ is reacted with a reagent Y"Z to the corresponding compound Pg-X—C[(CH$_2$)$_n$—YZ]$_3$.

Suitable protective groups are described above. It is known to persons skilled in the art how to introduce these protective groups and remove them again. Persons skilled in the art are able to apply this knowledge without leaving the scope of protection of the patent claims.

The purification of the reaction product occurs, by way of example by removing the solvent, adding the residue to a mixture comprising a polar aprotic solvent such as ethyl acetate and a diluted mineral acid, e.g. diluted hydrochloric acid, washing with a saturated KHSO$_4$ solution and drying.

In an advantageous embodiment, Y"Z is a catecholamine selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. In this case, X—C[(CH$_2$)$_n$—Y']$_3$ or Pg-X—C[(CH$_2$)$_n$—YZ]$_3$ is reacted with the catecholamine in the presence of an activating reagent and a coupling additive. Y' is hereby a carboxylic acid residue or a derivative thereof. Suitable activating reagents are, by way of example, EDC, DCC, DCl, PyClop, HBTU, HATU, HOSu, TBTU, T3P, BopCl and 3-Cl-1-pyridinium iodide. The substances HOBT, HOAt, HONB and NHS known to persons skilled in the art are usable, by way of example, as coupling additives. It is known to persons skilled in the art that these reactions are appropriately carried out with the addition of a base such as DIPEA. Persons skilled in the art are furthermore aware of different solvents to be used in the methods mentioned. They are able to independently produce these combinations of activating reagents, coupling additives, bases and solvents using their conventional knowledge and standard literature.

If the catecholamine Y"Z is adrenaline or noradrenaline, their aliphatic hydroxy group is optionally protected from the coupling with a protective group. The carboxyl group of the dihydroxyphenylalanine is equally suitable to be protected from the coupling if it represents Y"Z.

If a protective group Pg has been introduced and/or protected adrenaline, noradrenaline or dihydroxyphenylalanine has been used, these protective groups are removed at the end, and the deprotected product is subsequently purified.

In another advantageous embodiment, Y"Z is 3,4-dihydroxybenzoic acid or a similar derivative such as 3,4-dihydroxycinnamic acid or gallic acid. In this case, X—C[(CH$_2$)$_n$—Y']$_3$ or Pg-X—C[(CH$_2$)$_n$—Y']$_3$ is reacted with 3,4-dihydroxybenzoic acid, 3,4-dihydroxycinnamic acid or gallic acid in the presence of an activating reagent and a coupling additive. Y' is hereby advantageously an alcohol or amine function.

Suitable activating reagents are, by way of example, EDC, DCC, DCl, PyClop, HBTU, HATU, HOSu, TBTU, T3P, BopCl and 3-Cl-1-pyridinium iodide. The substances HOBT, HOAt and HONB known to persons skilled in the art are usable, by way of example, as coupling additives. It is known to persons skilled in the art that these reactions are appropriately carried out with the addition of a base such as DIPEA. Persons skilled in the art are furthermore aware of different solvents to be used in the methods mentioned. They are able to independently produce these combinations of activating reagents, coupling additives, bases and solvents using their conventional knowledge and standard literature.

In another advantageous embodiment, Y"Z is a catecholamine, selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. X—C[(CH$_2$)$_n$—Y']$_3$ or Prot-X—C[(CH$_2$)$_n$—Y']$_3$ is reacted with the catecholamine in the presence of a means of reduction. Y' is hereby an aldehyde or a ketone. Suitable means of reduction are, by way of example, NaBH$_4$, NaBH$_3$CN, NaBH(OAc)$_3$, as well as H$_2$ and metal catalysts. Persons skilled in the art know different solvents to be used in the methods mentioned. They are able to independently produce these combinations of means of reduction and solvents using their conventional knowledge and standard literature.

In another advantageous embodiment, Y"Z is a catecholamine, selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. X—C[(CH$_2$)$_n$—Y']$_3$ or Prot-X—C[(CH$_2$)$_n$—Y']$_3$ with a suitable leaving group Y' is reacted with the catecholamine. Suitable leaving groups are, by way of example, —OTs, OMs, —OTf and halides. Persons skilled in the art know different solvents to be used in the methods mentioned. They are able to independently produce these combinations of leaving groups and solvents using their conventional knowledge and standard literature.

In another advantageous embodiment, Y"Z is a catecholamine, selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. X—C[(CH$_2$)$_n$—Y']$_3$ or Pg-X—C[(CH$_2$)$_n$—Y']$_3$ is reacted with the catecholamine. Y' is hereby an isothiocyanate or an isocyanate. Persons skilled in the art know different solvents to be used in the methods mentioned. They are able to independently produce these combinations of means of reduction and solvents using their conventional knowledge and standard literature.

In a further advantageous embodiment, Y"Z is 3,4-dihydroxybenzaldehyde. X—C[(CH$_2$)n-Y']$_3$ or Pg-X—C[(CH$_2$)n-Y']$_3$ is reacted with 3,4-dihydroxybenzaldehyde. Y' is hereby an O-alkylhydroxylamine or the corresponding hydrohalide. Persons skilled in the art know different solvents to be used in the methods mentioned. They are able to independently produce these combinations of means of reduction and solvents using their conventional knowledge and standard literature.

In another advantageous embodiment, Y"Z is 3,4-dihydroxybenzoic acid or a similar derivative such as 3,4-dihydroxycinnamic acid or gallic acid. X—C[(CH$_2$)$_n$—Y']$_3$ oder Pg-X—C[(CH$_2$)$_n$—Y']$_3$ is reacted with 3,4-dihydroxybenzoic acid or a similar derivative such as 3,4-dihydroxycinnamic acid or gallic acid in the presence of an activating reagent such as DCC or EDC or with catalytic amounts of an acid such as HCl, H$_2$SO$_4$ or p-toluenesulfonic acid. Y' is hereby advantageously an alcohol function. Persons skilled in the art know different solvents to be used in the methods mentioned. They are able to independently produce these combinations of activating reagents, coupling additives, bases and solvents using their conventional knowledge and standard literature.

The compounds according to formula (I) according to the present invention are suitable to be used in a method to functionalise surfaces. The functionalisation hereby occurs via dip and rinse by dipping the surfaces to be functionalised into a solution of the compounds according to the present invention.

The compounds according to the present invention are advantageously dissolved in an aqueous buffer solution which comprises a salt concentration significantly higher than physiological salt concentrations (0.9 wt.-% of NaCl). MOPS (3(N-morpholine)-propane sulfonic acid) is, by way of example, a suitable buffer. NaCl and K$_2$SO$_4$ and mixtures thereof are suitable salts. The salt concentration advantageously amounts to between 10 and 20 wt.-% and the buffer concentration to between 0.05 and 0.2 mmol.

The X group of the compounds according to the present invention is suitable to be optionally coupled to an effector. The coupling of X to the effector is hereby suitable to be carried out both in solution, i.e. before the functionalisation of the surface, as well as on the surface, i.e. after the functionalisation of the surface. Effectors are, by way of example, ether groups, ester groups, heteroaromatic compounds, dyes, metal complexes, polymers (for example polyethylene glycols), pharmaceutical active agents (for example antibiotics, bisphosphonates), biomolecules (for example an amino acid), peptides, carbohydrates and terpenes. If the effector is a polymer and if this is a polyethylene glycol, it is advantageously a grouping —(O—CH$_2$—CH$_2$)$_q$—R$^5$ or —(CH$_2$—CH$_2$—O)$_q$—R$^5$, wherein q is a number between 1 and 10 and R$^5$ is defined as described under formula 1.

In an advantageous embodiment, the coupling of X is carried out by means of click chemistry. "Click reactions" are understood by persons skilled in the art to be energetically favoured reactions which run specifically and result in a single product. These are efficient reactions which are suitable to be carried out very easily. Click reactions are used in molecular biology, the development of active agents, biotechnology, macromolecular chemistry and material sciences. The concept of the click reaction was established by K. Barry Sharpless and describes reactions which are structured in a modular manner,
comprise a wide scope of application,
are suitable to be carried out with high yields,
occur stereospecifically,
allow for simple reaction conditions (as non-sensitive as possible against water and oxygen),
occur in environmentally-friendly solvents and/or solvents which are easily removable, such as water, or occur in a solvent-free manner,
require simple purification (extraction, phase separation, distillation or crystalisation) or no purification at all.

"Click reactions" are, in general, strongly thermodynamically favoured. This is frequently more than 84 kJ/mol, which results in a fast reaction with high selectivity for a single product. These are frequently carbon-heteroatom bond formations.

Chemical reactions which fulfill these criteria are:
the carbonyl chemistry of the "non-aldol type", such as the formation of urea, thiourea, oximes, imines, aromatic heterocycles and hydrazones, and the formation of carbamides and amides,
cyclo additions to unsaturated C—C bonds, in particular 1,3-dipolar cyclo additions such as the Huisgen cycloaddition, and also Diels-Alder reactions,
nucleophilic substitutions, in particular the ring opening of strained, electrophilic heterocycles such as aziridines and epoxides,
addition reactions at C—C multiple bonds, mostly in an oxidative manner such as, by way of example epoxidation, aziridination or dihydroxylation, but also Michael additions of Nu-H, wherein Nu is a nucleophile.

In another advantageous embodiment, the coupling of the effector to the X group occurs via conventional substitution or addition reactions which do not belong to the abovementioned conditions of a click reaction. These conventional reactions comprise, by way of example, the formation of ether, the esterification of a carboxylic acid or the formation of amide.

Particularly advantageously, the surfaces to be functionalised are metallic surfaces comprising iron and/or titanium or surfaces comprising apatite. It is known to persons skilled in the art that bones of vertebrates comprise approximately 50% apatite, approximately 70% dentine and more than 95% tooth enamel. Modern dental prostheses, such as dental fillings and implants, frequently comprise apatite and/or devices which comprise iron and/or titanium. It is furthermore known that the surfaces of endosprostheses, for example for hip and knee joints, comprise iron and/or titanium. The compounds according to the present invention according to formula (I) as well as the compounds which are suitable to be obtained from them and coupled to an effector, are therefore suitable for the surface functionalisation of dental and joint endosprotheses.

PRACTICAL EMBODIMENTS

Practical Embodiment 1

Production of 4-[2-(3,4-dihydroxyphenethylaminocarbonyl)ethyl]-N1,N7-bis(dihydroxyphenethyl)-4-(propiolacid amide)heptanediamide 5

Synthesis Plan:

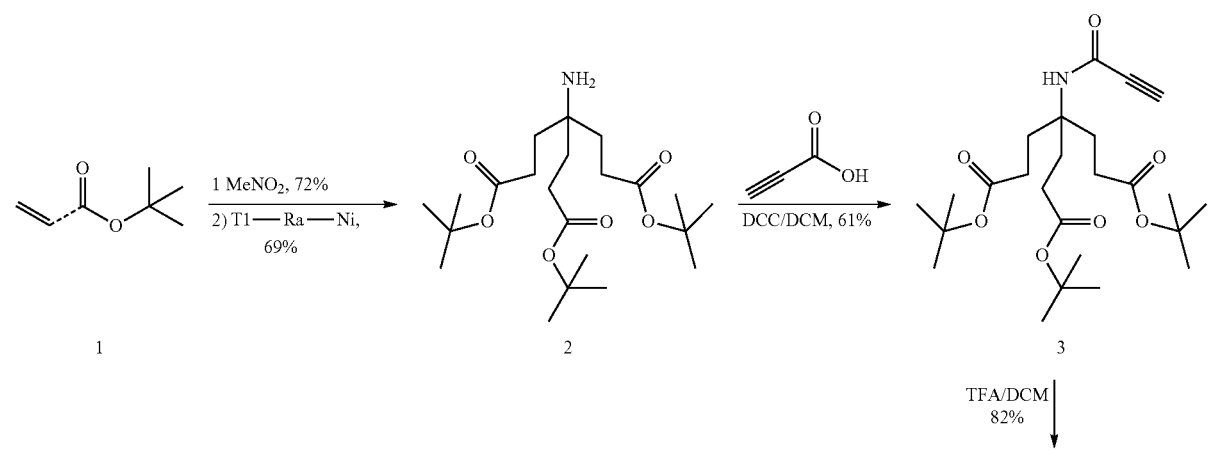

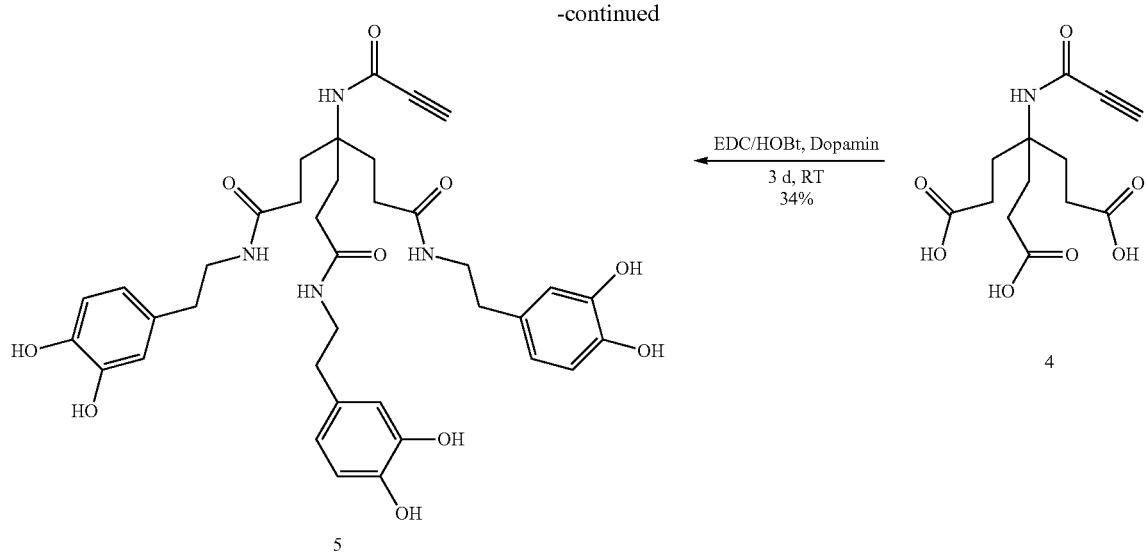

The tricarboxylic acid 4 (0.32 g, 1.10 mmol) and EtN$_3$ (1.44 mL; 10.4 mmol) were dissolved in abs. DMF and cooled to 0° C. After adding EDC (0.67 g, 4.3 mmol) and HOBt (0.58 g, 4.3 mmol), the reaction mixture was stirred for 30 min. Subsequently, the dopamine (0.65 g, 4.3 mmol) and EtN$_3$ (0.91 mL, 6.6 mmol) dissolved in DMF were added dropwise and stirred for 3 d at room temperature. After acid-base extraction and freeze drying, the resulting crude product was stirred several times in Et20 in order to remove the HOBt. The triscatechol 5 (0.06 g, 0,085 mmol, 8%) was obtained as colourless solid.

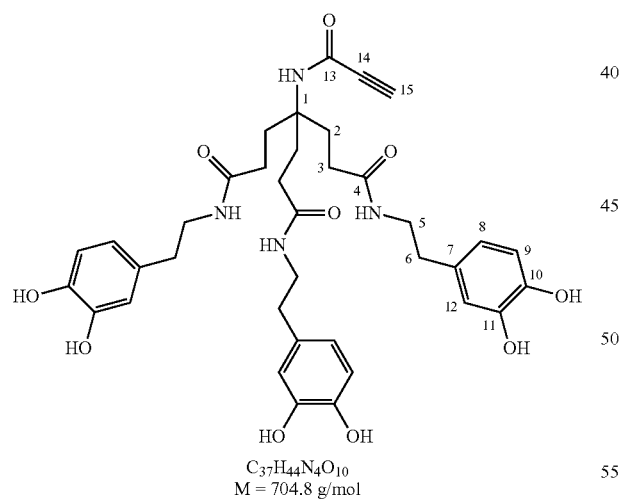

$C_{37}H_{44}N_4O_{10}$
M = 704.8 g/mol $^1$H-NMR (400 MHz, MeOH): δ [ppm]=6.68 (d, 3H, $^3$J=7.9 Hz, 9-H), 6.64 (s, 3H, 12-H), 6.52 (d, 3H, $^3$J=7.9 Hz, 8-H), 3.51 (s, 1H, 15-H), 3.34 (m, 6H, 6-H), 2.63 (t, 6H, $^3$J=7.1 Hz 5-H), 2.12 (s, 6H, 3-H), 2.13-2.09 (m, 6H, 3-H), 1.94-1.92 (m, 6H, 2-H); $^{13}$C-NMR (100 MHz, MeOD): δ [ppm]=175.5 (C4), 146.2 (C11), 144.8 (C10), 130.2 (C12), 121.1 (C8), 117.0 (C9), 116.4 (C7), 74.6 (C15), 60.3 (C1), 42.4 (C5), 34.8 (C6), 31.5 (C3), 31.2 (C2); HRMS (ESI): calculated for $C_{37}H_{44}N_4O_{10}$ [M+Na$^+$]=727.2955. found: 727.2961.

Practical Embodiment 2
4-[2-(3,4-dihydroxyphenethylaminocarbonyl)ethyl]-N1,N7-bis(dihydroxyphenethyl)-4-aminoheptanediamide 10
Synthesis Plan:
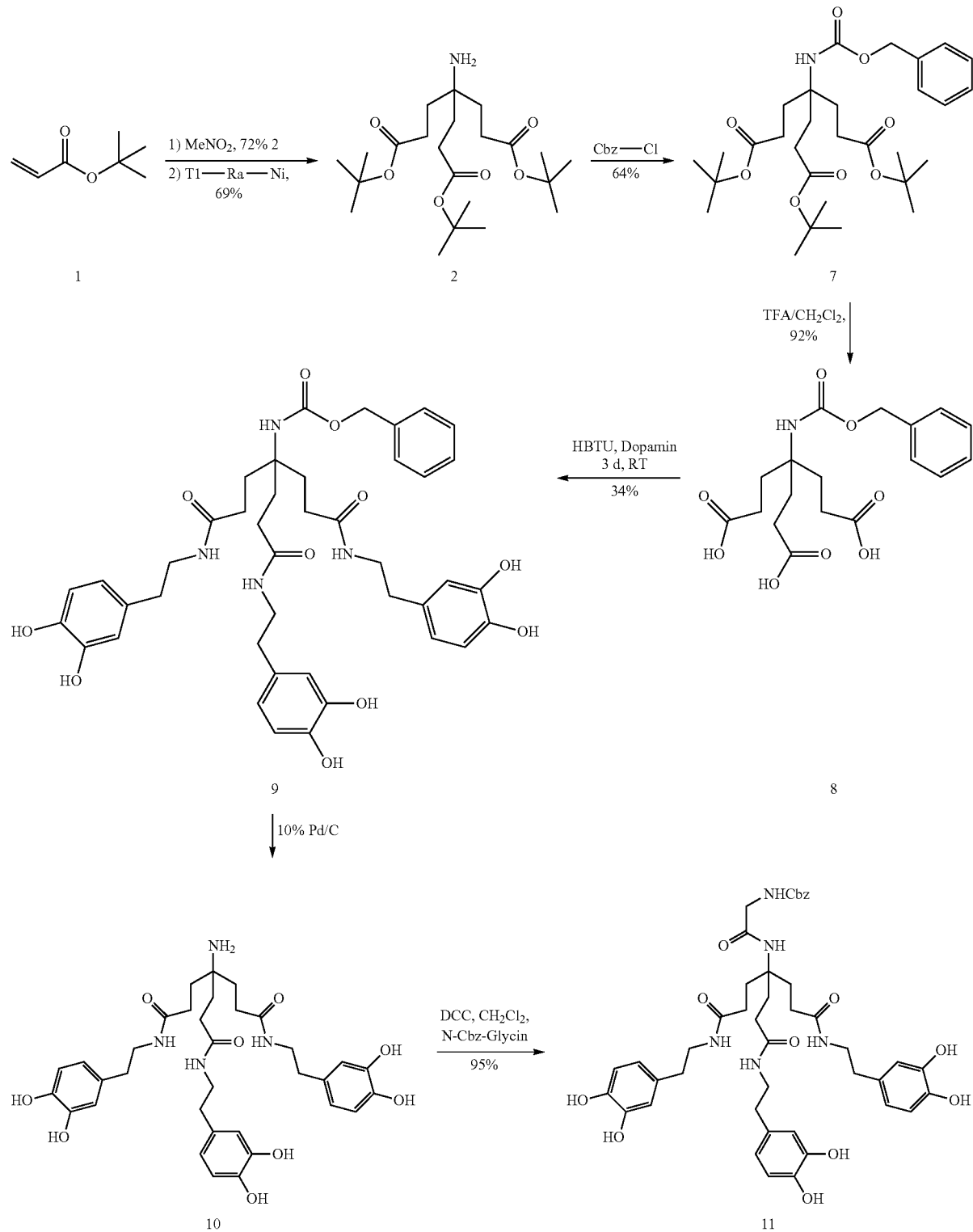

a) Di-tert-butyl-4-benzyloxycarbonyl-4-[2-(tert-butoxycarbonyl)ethyl]-heptane-dioate 7

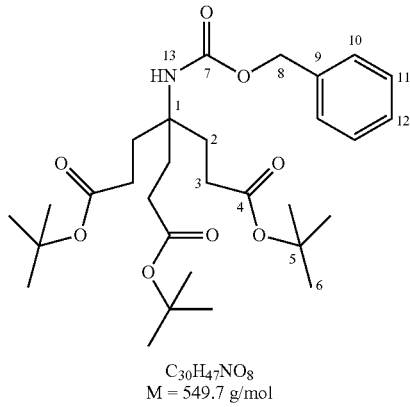 [SMILES: CC(C)(C)OC(=O)CCC(CCC(=O)OC(C)(C)C)(CCC(=O)OC(C)(C)C)NC(=O)OCc1ccccc1]

C$_{30}$H$_{47}$NO$_8$
M = 549.7 g/mol

The amine 2 (3.0 g, 7.2 mmol) was dissolved at room temperature in dioxane/H$_2$O (100 mL; 1:1) and cooled to 0° C., and NaHCO$_3$ (0.7 g, 8.3 mmol) was added. Subsequently, Cbz-Cl (1.4 g, 1.2 mL, 8.3 mmol) was added at 0° C. over 10 min. The reaction solution was stirred for 2 h at 0° C. and subsequently for 2 h at room temperature. It was extracted four times with CH$_2$Cl$_2$, and the unified organic phases were washed with aqueous 1 N HCl and dried over Na$_2$SO$_4$. After removal of the solvent in the vacuum, the crude product was purified via column chromatography. A colourless solid of the Cbz-protected amine 7 (2.5 g, 4.6 mmol, 64%) was obtained as product.

Smp.: 100° C.; R$_f$=0.42 (PE/EtOAc; 8.5:1.5); Cersulfat; $^1$H-NMR (400 MHz, CDCl$_3$): δ [ppm]=7.37-7.30 (m, 5H, 10-H, 11-H, 12-H), 5.04 (s, 2H, 8-H), 4.83 (s, 1H, 13-H), 2.20 (t, 6H, $^3$J=7.52 Hz, $^3$J=8.26 Hz, 3-H), 1.91 (t, 6H, $^3$J=8.24 Hz, $^3$J=7.43 Hz, 2-H), 1.43 (s, 27H, 6-H); $^{13}$C-NMR (100 MHz, CDCl$_3$): δ [ppm]=172.7 (C4), 154.3 (C7), 136.7 (C9), 128.6 (C10), 128.2 (C11), 128.1 (C12), 80.7 (C5), 66.3 (C8), 56.7 (C1), 30.2 (C3), 29.8 (C2), 28.2 (C6); IR (KBr pressling): ν [cm$^{-1}$]=3348, 1726, 757; HRMS (ESI): calculated for C$_{30}$H$_{47}$NO$_8$ [M+Na+]=572.3199. found: 572.3195; CHN analysis. found (calculated) [%]: C=65.63 (65.55), H=8.65 (8.62), N=2.55 (2.55).

b) 4-benzyloxycarbonyl-4-(2-carboxyethyl)-heptane diacid 8

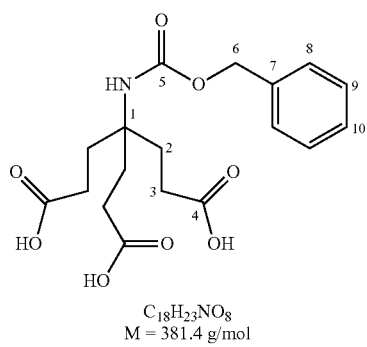 [SMILES: O=C(O)CCC(CCC(=O)O)(CCC(=O)O)NC(=O)OCc1ccccc1]

C$_{18}$H$_{23}$NO$_8$
M = 381.4 g/mol

The trimester 7 (2.0 g, 3.6 mmol) was dissolved in TFA (45 mL) and CH$_2$Cl$_2$ (135 mL) and stirred for 4 h at room temperature. Subsequently, it was coevaporated five times with CH$_2$Cl$_2$, and the solvent was distilled off under vacuum. The residue was taken up in EtOAc and aqueous 1 N HCl and washed three times with aqueous 1 N HCl, and the unified organic phases were dried over Na$_2$SO$_4$. After removal of the solvent under vacuum, the tricarboxylic acid 8 (1.3 g, 3.3 mmol, 92%) was obtained as colourless solid.

$^1$H-NMR (400 MHz, DMSO): δ [ppm]=7.32-7.29 (m, 5H, 8-H, 9-H, 10-H), 4.98 (s, 2H, 6-H), 2.12 (t, 6H, $^3$J=7.78 Hz, $^3$J=7.83 Hz, 3-H), 1.79 (t, 6H, $^3$J=8.38 Hz, $^3$J=7.78 Hz, 2-H); $^{13}$C NMR (100 MHz, DMSO): δ [ppm]=174.5 (C4), 154.3 (C5), 137.5 (C7), 128.4 (C8), 127.7 (C9), 127.5 (C10), 64.7 (C6), 55.8 (C1), 29.2 (C3), 28.1 (C2); IR (KBr pressling): ν [cm$^{-1}$]=3433, 1712, 697; HRMS (ESI): calculated for C$_{18}$H$_{23}$NO$_8$ [M+Na$^+$]=404.1321. found: 404.1326; CHN analysis. found (calculated) [%]: C=52.46 (56.69), H=6.17 (6.08), N=3.34 (3.67).

c) 4-benzyloxycarbonyl-4-[2-(3,4-dihydroxyphenethylaminocarbonyl)ethyl]-N1,N7-bis-(dihydroxyphenethyl)-4-heptanediamide 9

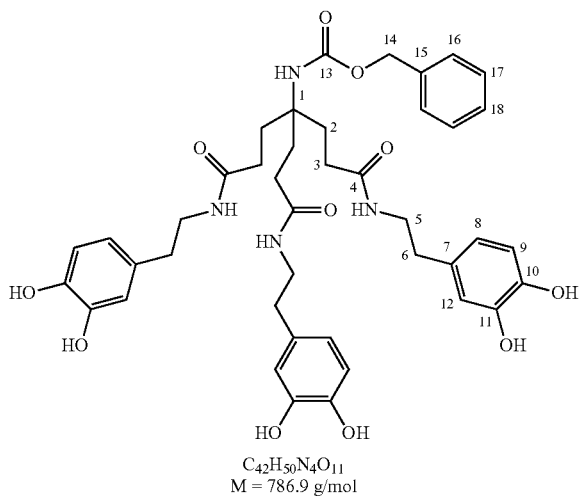 [SMILES: O=C(CCC(CCC(=O)NCCc1ccc(O)c(O)c1)(CCC(=O)NCCc1ccc(O)c(O)c1)NC(=O)OCc1ccccc1)NCCc1ccc(O)c(O)c1]

C$_{42}$H$_{50}$N$_4$O$_{11}$
M = 786.9 g/mol

The tricarboxylic acid 8 (0.20 g, 0.52 mmol) was reacted with dopamine (0.26 g, 1.72 mmol) in DMF (20 mL) according to AAVX. After freeze drying, the resulting crude product was stirred three times in Et$_2$0 in order to remove the HOBt obtained. After decanting the Et$_2$O, the coupled product 9 (0.14 g, 0.18 mmol, 34%) was obtained as colourless solid.

$^1$H-NMR (400 MHz, CDCl$_3$): δ [ppm]=7.35-7.30 (m, 5H, 16-H, 17-H, 18-H), 6.60 (d, 3H, $^3$J=7.87 Hz, 9-H), 6.57 (s, 3H, 12-H), 6.42 (d, 3H, $^3$J=7.87 Hz, 8-H), 5.00 (s, 2H, 14-H), 3.41-3.36 (m, 6H, 5-H), 3.15-3.14 (m, 6H, 6-H), 2.00 (s, 6H, 3-H), 1.78 (s, 6H, 2-H); $^{13}$C-NMR (100 MHz, CDCl$_3$): δ [ppm]=172.0 (C4), 145.1 (C11), 143.5 (C10), 137.4 (C15), 130.3 (C7), 128.4 (C16), 127.7 (C17), 127.5 (C18), 64.9 (C14), 56.2 (C1), 40.7 (C5), 34.8 (C3), 30.4 (C6), 29.7 (C2); HRMS (ESI): calculated for C$_{42}$H$_{50}$N$_4$O$_{11}$ [M+Na$^+$]=809.3374. found: 809.3374.

d) 4-[2-(3,4-dihydroxyphenethylaminocarbonyl) ethyl]-N1,N7-bis(dihydroxyphenethyl)-4-aminoheptanediamide 10

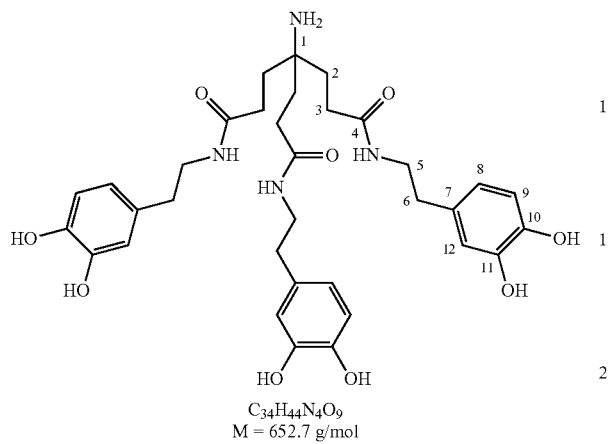

$C_{34}H_{44}N_4O_9$
M = 652.7 g/mol

The coupled product 9 (0.035 g, 0.044 mmol) was dissolved in abs. MeOH (10 mL) and reacted according to AAVX. After filtration, the amine 10 as crude product (0.035 mg) was obtained brown oil.

$^1$H-NMR (400 MHz, CDCl$_3$): δ [ppm]=7.35-7.30 (m, 5H, 16-H, 17-H, 18-H), 6.47 (d, 3H, $^3$J=7.93 Hz, 9-H), 6.56 (s, 3H, 12-H), 6.42 (d, 3H, $^3$J=7.93 Hz, 8-H), 3.17 (s, 12H, 5-H, 6-H), 2.07 (s, 6H, 3-H), 1.52 (s, 6H, 2-H); $^{13}$C-NMR (100 MHz, CDCl$_3$): δ [ppm]=172.0 (C4), 145.0 (C11), 143.5 (C10), 130.2 (C7), 119.1 (C12), 115.9 (C9), 115.4 (C8), 48.6 (C1), 40.6 (C5), 34.6 (C3), 34.0 (C6), 29.7 (C2); HRMS (ESI): calculated for $C_{34}H_{44}N_4O_9$ [M+Na+]=653.3187. found: 653.3196.

e) 4-benzyloxycarbonyl-glycine-4-[2-(3,4-dihydroxyphenethylaminocarbonyl)ethyl]-N1,N7-bis-(dihydroxyphenethyl)-4-heptanediamide 11

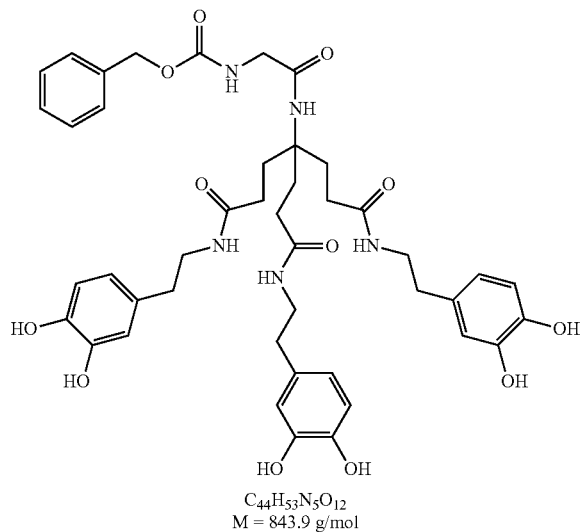 [SMILES: O=C(CCC(CCC(=O)NCCc1ccc(O)c(O)c1)(CCC(=O)NCCc1ccc(O)c(O)c1)NC(=O)CNC(=O)OCc1ccccc1)NCCc1ccc(O)c(O)c1]

$C_{44}H_{53}N_5O_{12}$
M = 843.9 g/mol

The amine 10 (3.8 g, 9.1 mmol) was dissolved at 0° C. in abs. CH$_2$Cl$_2$ (100 mL), and Cbz-Glycine (2.8 g, 13.6 mmol), dissolved in abs. CH$_2$Cl$_2$ (50 mL), was added. Subsequently, DCC (2.8 g, 13.6 mmol) was added and stirred at room temperature for 24 h. The precipitated DCU was filtered off, the CH$_2$Cl$_2$ removed in the vacuum, and the residue taken up with EtOAc. The reaction solution was washed twice with a saturated aqueous KHSO$_4$ solution and twice with a saturated aqueous NaCl solution. The unified organic phases were dried over Na$_2$SO$_4$, and EtOAc was removed in the vacuum. The Cbz-glycine coupled triscatechol 11 (5.2 g, 8.5 mmol, 95%) was obtained as colourless solid.

MS (ESI): m/z (%)=866.5 (58) [M+Na$^+$], 844.3 (50) [M+H$^+$].

Practical Embodiment 3

4-[2-(3,4-dihydroxyphenethylaminocarbonyl)ethyl]-$N^1$,$N^7$-bis(dihydroxyphenethyl)-4-nitroheptanediamide 13

Synthesis Plan:

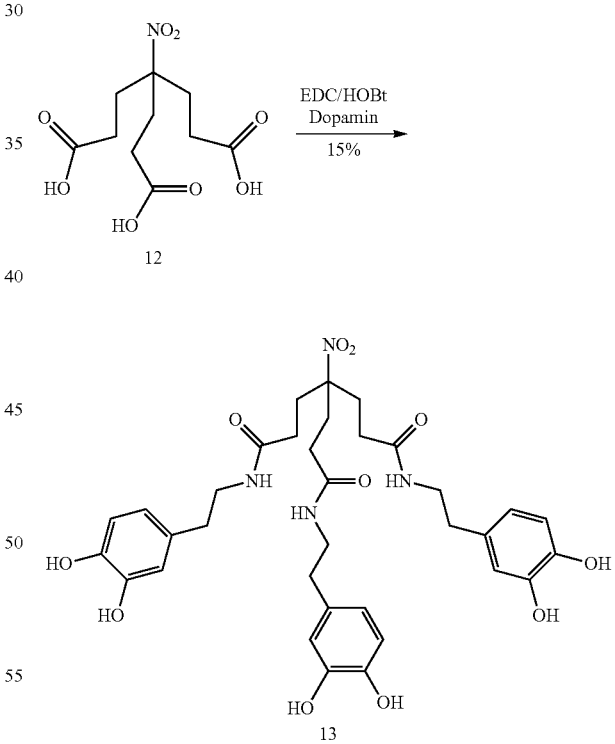

The tricarboxylic acid 4 12 (0.1 g, 0.36 mmol) and EtN$_3$ (0.47 mL; 3.40 mmol) were dissolved in abs. DMF (10 mL) and cooled to 0° C. After addition of EDC (0.25 g, 1.62 mmol) and HOBt (0.22 g, 1.62 mmol), reaction mixture was stirred for 5 min. Subsequently, the dopamine (0.25 g, 1.62 mmol) and EtN$_3$ (0.47 mL, 3.40 mmol) dissolved in DMF were added dropwise and stirred for 3 d at room temperature. The DMF was removed in the vacuum and the residue washed with aqueous 1 N HCl solution and the organic phase dried over Na$_2$SO$_4$. After freeze drying, the crude product was stirred several times in Et$_2$O in order to remove the HOBt obtained. The triscatechol 13 (0.04 g, 0.06 mmol, 15%) was obtained as colourless solid.

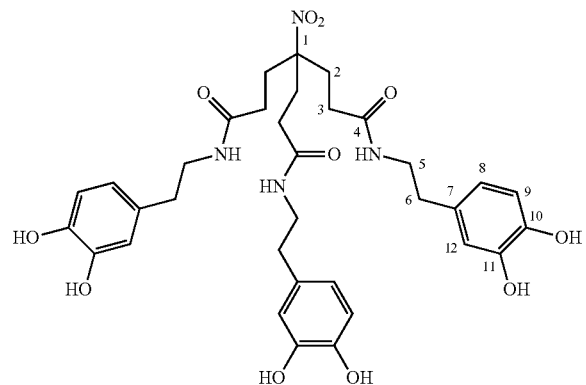 [SMILES: O=C(CCC(CCC(=O)NCCc1ccc(O)c(O)c1)(CCC(=O)NCCc1ccc(O)c(O)c1)[N+](=O)[O-])NCCc1ccc(O)c(O)c1]

$^1$H-NMR (400 MHz, CH$_3$OD): δ [ppm]=6.68 (d, 3H, $^3$J=8.0 Hz, 9-H), 6.6 (d, 3H, $^4$J=2.0 Hz 12-H), 6.50 (dd, 3H, $^3$J=8.1 Hz, $^4$J=2.0 Hz, 8-H), 3.34-3.30 (m, 6H, 6-H), 2.63 (t, 6H, $^3$J=7.4 Hz, 5-H), 2.16-2.09 (m, 12H, 2-H, 3-H); MS (ESI): m/z (%)=705.3 (85) [M+Na$^+$].

Practical Embodiment 4

Surface Modification

For the surface modification, TiO$_2$ surfaces on Si wafers are used. For that purpose, a solution from TiCl$_4$, water and ethanol is produced, and the Si wafers are dipped in and extracted at a speed of 1 mm/sec. In the oven, the surfaces are "burnt" into their final form. For that purpose, the Si wafers are heated to 80° C. over 6 h, then for 6 h to 300° C., and then with a heating rate of 10° C./min to 550° C.

The compounds (5 mg each) according to the present invention are dissolved in 5 mL MeOH and 15 mL pure HPLC water.

For the dipcoating method, 100 mL buffer stock solution (0.1 mol/Mops) is produced from 3.5 g NaCl, 10.45 g K$_2$SO$_4$ and 2.31 g Mops (=3-morpholinopropane-1-sulfonic acid). For that purpose, also pure HPLC water is used.

5 mL of the solvent of each compound according to the present invention and 10 mL buffer stock solution are mixed and the TiO$_2$ surfaces are coated by means of dip-coating for 13 h.

After this reaction time the surfaces are purified with distilled MeOH and distilled water, dried by means of air pressure and measured by means of contact angle measurement and SIMS-Tof.

Practical Embodiment 5

Contact Angle Measurement

The following substances have been measured:

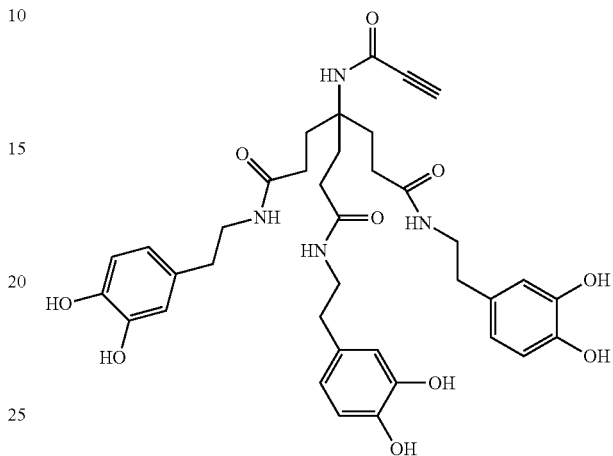

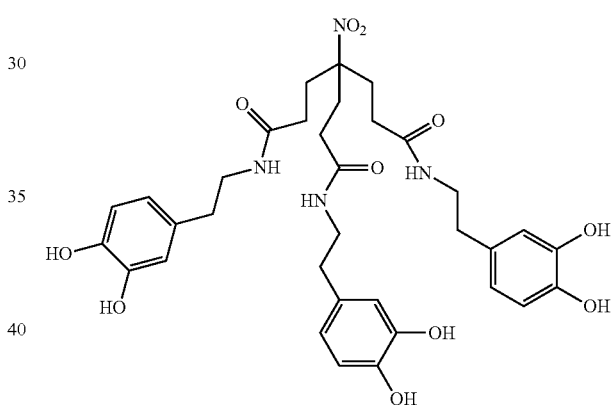

Before each measurement, the TiO$_2$ surfaces to be measured are purified from dust and drops of water by means of air pressure.

A contact angle measurement device (Krüss Dropshape Analyser, DAS 10-MK 2) was used for the measurement, wherein a constant temperature of 23° C. was obtained in the measurement chamber. A needle which produced a drop of water (HPLC grade water) of 4 µl was driven slowly to the surface in order to displace the drop onto the surface.

From this point onwards, a camera took a sequence of 1,000 photos which were manually analysed at the end with the help of specific computer software (Krüss, DSA=Drop Shape Analyse) which uses the Young-Laplace method (Sessel Drop Fitting).

Each TiO$_2$ surface was measured 3 to 4 times, and the mean value was determined from the results.

A pure, purified TiO$_2$ sheet without coating (second column in table 1) and the TiO$_2$ sheet coated with Mops buffer (column 3 in table 1) were measured as controls, respectively. Column 4 shows the results of the contact angle measurements of TiO$_2$ sheets, which had been coated with 5 and 11 ("molecules") substances dissolved in MOPS buffer.

TABLE 1

Results of the contact angle measurement

| Substance no. | $TiO_2$ Contact angle (°) | $TiO_2$ + Mops Contact angle (°) | $TiO_2$ + Mops + molecules Contact angle (°) |
|---|---|---|---|
| 5 | 27.9 | 8.1 | 18.5 |
| 11 | 32.3 | 5.8 | 22.9 |

The invention claimed is:

1. A compound according to formula (I)

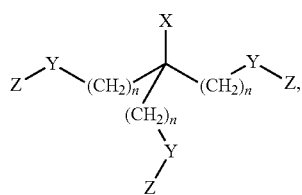

wherein
 n is an integer between 0 and 10,
 Y is a bond, —$CH_2$—, —$NR^1$—, —NH—(C=O)—, or —(C=O)—NH—
 $R^1$ is a linear alkyl group with 1 to 10 C atoms, or for a branched or cyclic alkyl group with 3 to 10 C atoms,
 Z is selected from

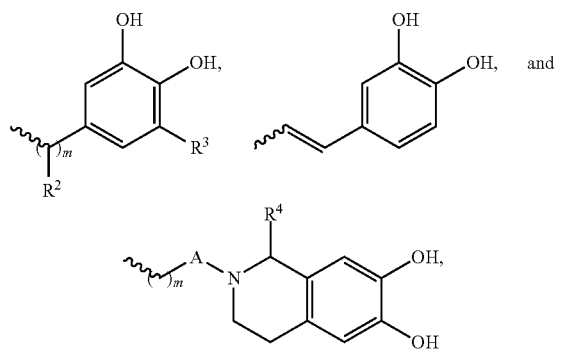

m is an integer between 0 and 10,
 $R^2$ is —H, —OH or —COOH,
 $R^3$ is —H or —OH,
 A is a bond or —(C=O)—,
 $R^4$ is —H or

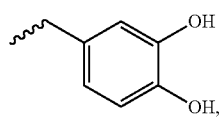

X is —$(CH_2)_p$—$R^5$; a branched alkyl, alkenyl or alkynyl group with 3 to 10 C atoms; a cyclic alkyl, alkenyl or alkynyl group with 3 to 10 C atoms; or an aryl or heteroaryl group,
 p is an integer between 0 and 10
 $R^5$ is —H, —$NH_2$, —$NO_2$, —OH, —SH, —O—$NH_2$, —NH—$NH_2$, —N=C=S, —NC=O, —CH=$CH_2$, —C≡CH, —COOH, —(C=O)H, or —(C=O)$R^6$, wherein the hydroxy, thio, amino or C=O groups are optionally protected by a protective group, —$N_3$, —$OR^6$, —$COOR^6$, —$NHR^6$, —$NR^6R^7$, —CO—$NHR^6$, —$CONR^6R^7$, —NH—CO—$R^6$, or 4-(2,5-dioxopyrrol-1-yl), and $R^6$ and $R^7$ each, independently, is a linear alkyl group with 1 to 10 C atoms, a linear alkenyl or alkynyl group with 2 to 10 C atoms, or a branched alkyl, alkenyl or alkynyl group with 3 to 10 C atoms, wherein, if X is a branched alkyl, alkenyl or alkynyl group, a cyclic alkyl or alkenyl group, an aryl or heteroaryl group, then one C atom of this group X is optionally substituted with $R^5$.

2. The compound according to claim 1, wherein n is an integer between 0 and 3.

3. The compound according to claim 1, m is an integer between 0 and 3.

4. The compound according to claim 1, wherein Z is

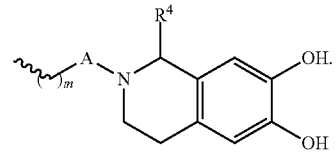

5. The compound according to claim 1, wherein the group YZ is selected from

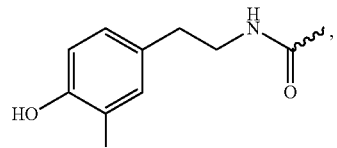

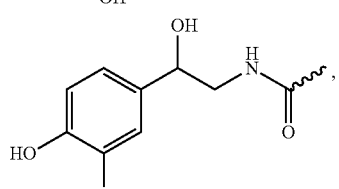

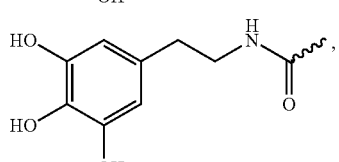

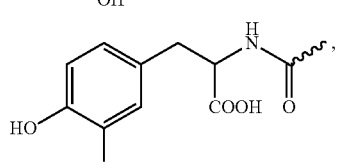

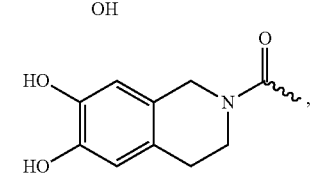

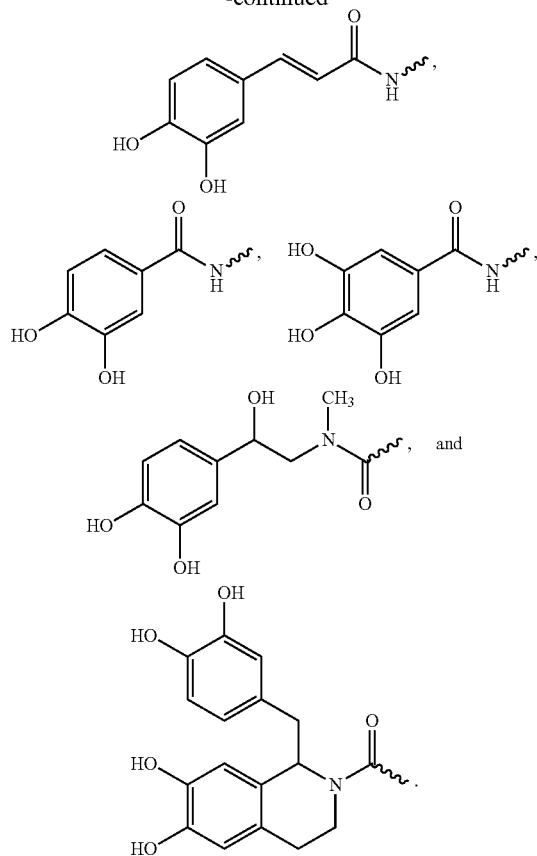

6. The compound according to claim 1, wherein X is —(CH$_2$)$_p$—R$^5$, and p is an integer between 0 and 3.

7. The compound according to claim 1, wherein
X is —(CH$_2$)$_p$—R$^5$,
R$^5$ is —H, —OH, —NH$_2$, —NO$_2$, —NH—NH$_2$, —NHR$^6$, —NR$^6$R$^7$, —O—NH$_2$, —NH—(C=O)—C≡CH, —C≡CH, —N=C=S, —N=C=O, —COOH, —(C=O)H, or —(C=O)R$^6$, and
p is an integer between 0 and 3.

8. A compound according to formula (I)

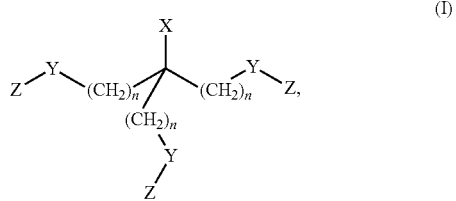

(I)

wherein
n is an integer between 0 and 10,
Y is a bond, —CH$_2$—, —CH=CH—, —C≡C—, —O—, —S—, —S—S—, —NH—, —O—NH—, —NH—O—, —HC=N—O—, —O—N=CH—, —NR$^1$—, -aryl-, -heteroaryl-, —(C=O)—, —O—(C=O)—, —(C=O)—O—, —NH—(C=O)—, —(C=O)—NH—, —NR$^1$—(C=O)—, —(C=O)—NR$^1$—, —NH—(C=O)—NH—, or —NH—(C=S)—NH—,
R$^1$ is a linear alkyl group with 1 to 10 C atoms, or for a branched or cyclic alkyl group with 3 to 10 C atoms, Z is

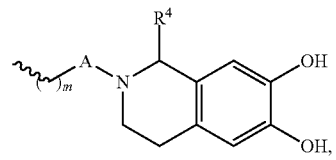

m is an integer between 0 and 10,
A is a bond or —(C=O)—,
R$^4$ is —H or

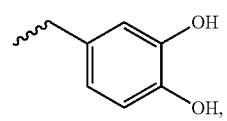

X is —(CH$_2$)$_p$—R$^5$; a branched alkyl, alkenyl or alkynyl group with 3 to 10 C atoms; a cyclic alkyl, alkenyl or alkynyl group with 3 to 10 C atoms; or an aryl or heteroaryl group,
p is an integer between 0 and 10
R$^5$ is —H, —NH$_2$, —NO$_2$, —OH, —SH, —O—NH$_2$, —NH—NH$_2$, —N=C=S, —NC=O, —CH=CH$_2$, —C≡CH, —COOH, —(C=O)H, or —(C=O)R$^6$, wherein the hydroxy, thio, amino or C=O groups are optionally protected by a protective group, —N$_3$, —OR$^6$, —COOR$^6$, —NHR$^6$, —NR$^6$R$^7$, —CO—NHR$^6$, —CONR$^6$R$^7$, —NH—CO—R$^6$, or 4-(2,5-dioxopyrrol-1-yl), and
R$^6$ and R$^7$ each, independently, is a linear alkyl group with 1 to 10 C atoms, a linear alkenyl or alkynyl group with 2 to 10 C atoms, or a branched alkyl, alkenyl or alkynyl group with 3 to 10 C atoms,
wherein, if X is a branched alkyl, alkenyl or alkynyl group, a cyclic alkyl or alkenyl group, an aryl or heteroaryl group, then one C atom of this group X is optionally substituted with R$^5$.

9. The compound according to claim 8, wherein Y is a bond, —CH$_2$—, —NH—(C=O)—, —(C=O)—NH—, or —NR$^1$.

10. The compound according to claim 8, wherein n is an integer between 0 and 3.

11. The compound according to claim 8, m is an integer between 0 and 3.

12. The compound according to claim 8, wherein the group YZ is selected from

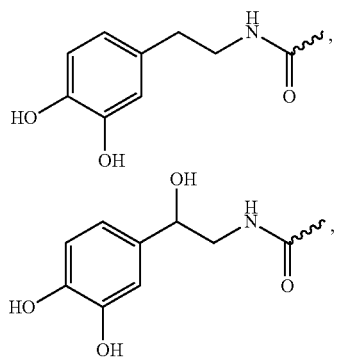

-continued
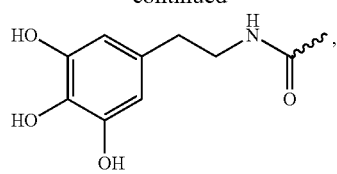
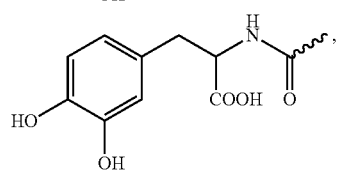
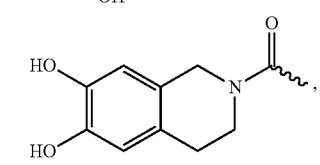
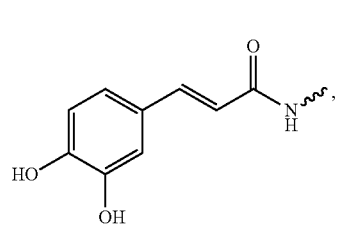
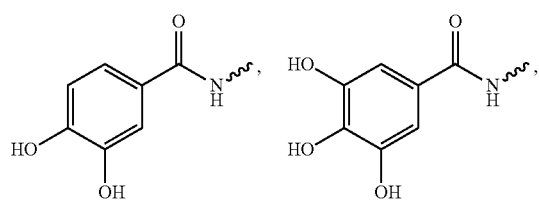
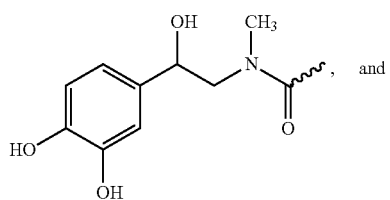 and
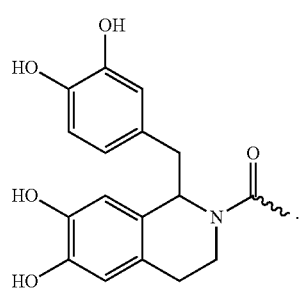
13. The compound according to claim 8, wherein X is —(CH$_2$)$_p$—R$^5$, and p is an integer between 0 and 3.
14. The compound according to claim 13, wherein R$^5$ is —H, —OH, —NH$_2$, —NO$_2$, —NH—NH$_2$, —NHR$^6$, —NR$^6$R$^7$, —O—NH$_2$, —NH—(C═O)—C≡CH, —C≡CH, —N═C═S, —N═C═O, —COOH, —(C═O)H, or —(C═O)R$^6$.
15. A compound according to formula (I)
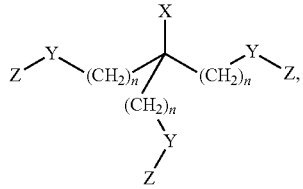
wherein
n is an integer between 0 and 10,
YZ is selected from
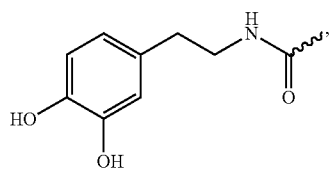
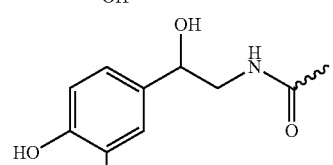
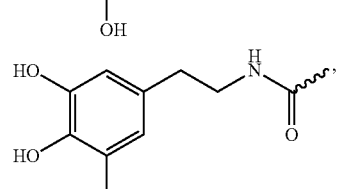
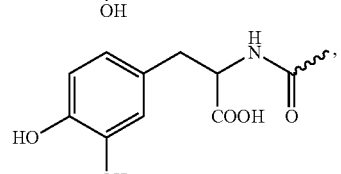
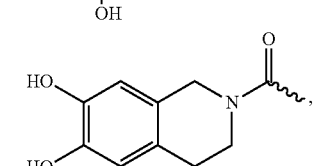
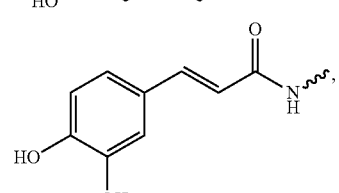
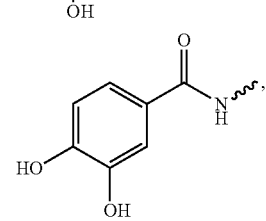

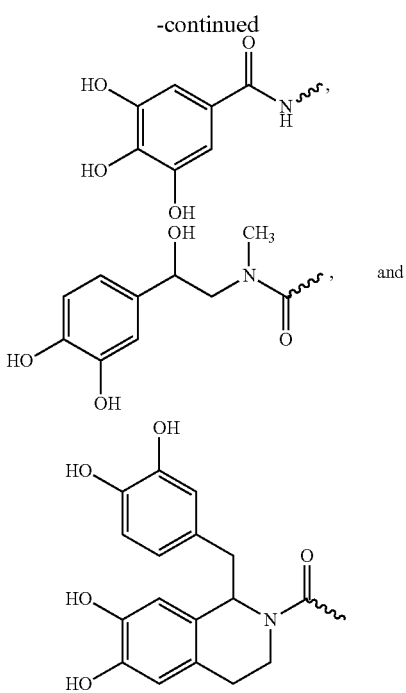

X is —(CH$_2$)$_p$—R$^5$; a branched alkyl, alkenyl or alkynyl group with 3 to 10 C atoms; a cyclic alkyl, alkenyl or alkynyl group with 3 to 10 C atoms; or an aryl or heteroaryl group, p is an integer between 0 and 10

R$^5$ is —H, —NH$_2$, —NO$_2$, —OH, —SH, —O—NH$_2$, —NH—NH$_2$, —N=C=S, —NC=O, —CH=CH$_2$, —C≡CH, —COOH, —(C=O)H, or —(C=O)R$^6$, wherein the hydroxy, thio, amino or C=O groups are optionally protected by a protective group, —N$_3$, —OR$^6$, —COOR$^6$, —NHR$^6$, —NR$^6$R$^7$, —CO—NHR$^6$, —CONR$^6$R$^7$, —NH—CO—R$^6$, or 4-(2,5-dioxopyrrol-1-yl), and R$^6$ and R$^7$ each, independently, is a linear alkyl group with 1 to 10 C atoms, a linear alkenyl or alkynyl group with 2 to 10 C atoms, or a branched alkyl, alkenyl or alkynyl group with 3 to 10 C atoms, wherein, if X is a branched alkyl, alkenyl or alkynyl group, a cyclic alkyl or alkenyl group, an aryl or heteroaryl group, then one C atom of this group X is optionally substituted with R$^5$.

16. The compound according to claim 15, wherein n is an integer between 0 and 3.

17. The compound according to claim 15, wherein X is —(CH$_2$)$_p$—R$^5$, and p is an integer between 0 and 3.

18. The compound according to claim 17, wherein R$^5$ is —H, —OH, —NH$_2$, —NO$_2$, —NH—NH$_2$, —NHR$^6$, —NR$^6$R$^7$, —O—NH$_2$, —NH—(C=O)—C≡CH, —C≡CH, —N=C=S, —N=C=O, —COOH, —(C=O)H, or —(C=O)R$^6$.

* * * * *